United States Patent
Squires et al.

(10) Patent No.: US 12,329,531 B2
(45) Date of Patent: *Jun. 17, 2025

(54) MAPPING ECG SIGNALS USING A MULTIPOLE ELECTRODE ASSEMBLY

(71) Applicant: Biosense Webster (Israel) Ltd., Yokneam (IL)

(72) Inventors: Alexander David Squires, Duarte, CA (US); Christopher Thomas Beeckler, Brea, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/534,675

(22) Filed: Nov. 24, 2021

(65) Prior Publication Data

US 2022/0079496 A1    Mar. 17, 2022

Related U.S. Application Data

(63) Continuation of application No. 16/235,769, filed on Dec. 28, 2018, now Pat. No. 11,207,016.

(51) Int. Cl.
*A61B 5/00* (2006.01)
*A61B 5/287* (2021.01)
*A61B 5/341* (2021.01)

(52) U.S. Cl.
CPC ............ *A61B 5/341* (2021.01); *A61B 5/0006* (2013.01); *A61B 5/287* (2021.01); *A61B 5/6858* (2013.01); *A61B 2562/046* (2013.01); *A61B 2562/125* (2013.01)

(58) Field of Classification Search
CPC .............................. A61B 5/287; A61B 5/6858
See application file for complete search history.

(56) References Cited

U.S. PATENT DOCUMENTS

| | | | |
|---|---|---|---|
| 4,660,571 A | 4/1987 | Hess et al. | |
| 4,699,147 A | 10/1987 | Chilson et al. | |
| 4,940,064 A | 7/1990 | Desai | |
| 5,215,103 A | 6/1993 | Desai | |

(Continued)

FOREIGN PATENT DOCUMENTS

| CN | 104720890 A | 6/2015 |
|---|---|---|
| CN | 102871727 N | 7/2015 |

(Continued)

OTHER PUBLICATIONS

Cantwell, C. D., et al. "Techniques for automated local activation time annotation and conduction velocity estimation in cardiac mapping" Computers in Biology and Medicine, pp. 1-17 (18 pages submitted) Apr. 2015.

(Continued)

*Primary Examiner* — John R Downey
*Assistant Examiner* — Anant A Gupta (57) ABSTRACT

A medical probe includes an insertion tube for insertion into a patient body, at least an arm, which is attached to a distal end of the insertion tube, at least a reference electrode coupled to the arm, and multiple electrodes, which are coupled to the arm, surround the reference electrode and are configured to sense electrical signals of body tissues that, when measured relatively to the reference electrode, are indicative of anatomical signals in the patient body.

17 Claims, 2 Drawing Sheets

(56) References Cited

U.S. PATENT DOCUMENTS

| | | |
|---|---|---|
| 5,255,679 A | 10/1993 | Imran |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,345,936 A | 9/1994 | Pomeranz et al. |
| 5,365,926 A | 11/1994 | Desai |
| 5,391,199 A | 2/1995 | Ben-Haim |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,456,254 A | 10/1995 | Pietroski et al. |
| 5,465,717 A | 11/1995 | Imran et al. |
| 5,476,495 A | 12/1995 | Kordis et al. |
| 5,482,037 A | 1/1996 | Borghi |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,553,611 A * | 9/1996 | Budd .................... A61B 5/0538 600/374 |
| 5,558,073 A | 9/1996 | Pomeranz et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 6,014,579 A | 1/2000 | Pomeranz et al. |
| 6,014,590 A | 1/2000 | Whayne et al. |
| 6,050,267 A | 4/2000 | Nardella et al. |
| 6,064,905 A | 5/2000 | Webster, Jr. et al. |
| 6,119,030 A | 9/2000 | Morency |
| 6,216,043 B1 | 4/2001 | Swanson et al. |
| 6,216,044 B1 | 4/2001 | Kordis |
| 6,239,724 B1 | 5/2001 | Doron et al. |
| 6,332,089 B1 | 12/2001 | Acker et al. |
| 6,428,537 B1 | 8/2002 | Swanson et al. |
| 6,456,864 B1 | 9/2002 | Swanson et al. |
| 6,484,118 B1 | 11/2002 | Govari |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,618,612 B1 | 9/2003 | Acker et al. |
| 6,690,963 B2 | 2/2004 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| RE41,334 E | 5/2010 | Beatty et al. |
| 7,846,157 B2 | 12/2010 | Kozel |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 9,037,264 B2 | 5/2015 | Just et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |

(56) References Cited

U.S. PATENT DOCUMENTS

| | | | |
|---|---|---|---|
| 10,403,053 B2 | 9/2019 | Katz et al. | |
| 10,441,188 B2 | 10/2019 | Katz et al. | |
| 10,470,682 B2 | 11/2019 | Deno et al. | |
| 10,470,714 B2 | 11/2019 | Altmann et al. | |
| 10,482,198 B2 | 11/2019 | Auerbach et al. | |
| 10,492,857 B2 | 12/2019 | Guggenberger et al. | |
| 10,542,620 B2 | 1/2020 | Weinkam et al. | |
| 10,575,743 B2 | 3/2020 | Basu et al. | |
| 10,575,745 B2 | 3/2020 | Solis | |
| 10,582,871 B2 | 3/2020 | Williams et al. | |
| 10,582,894 B2 | 3/2020 | Ben Zrihem et al. | |
| 10,596,346 B2 | 3/2020 | Aeby et al. | |
| 10,602,947 B2 | 3/2020 | Govari et al. | |
| 10,617,867 B2 | 4/2020 | Viswanathan et al. | |
| 10,660,702 B2 | 5/2020 | Viswanathan et al. | |
| 10,667,753 B2 | 6/2020 | Werneth et al. | |
| 10,674,929 B2 | 6/2020 | Houben et al. | |
| 10,681,805 B2 | 6/2020 | Weinkam et al. | |
| 10,682,181 B2 | 6/2020 | Cohen et al. | |
| 10,687,892 B2 | 6/2020 | Long et al. | |
| 10,702,178 B2 | 7/2020 | Dahlen et al. | |
| 10,716,477 B2 | 7/2020 | Salvestro et al. | |
| 10,758,304 B2 | 9/2020 | Aujla | |
| 10,765,371 B2 | 9/2020 | Hayam et al. | |
| 10,772,566 B2 | 9/2020 | Aujila | |
| 10,799,281 B2 | 10/2020 | Goertzen et al. | |
| 10,842,558 B2 | 11/2020 | Harlev et al. | |
| 10,842,561 B2 | 11/2020 | Viswanathan et al. | |
| 10,863,914 B2 | 12/2020 | Govari et al. | |
| 10,881,376 B2 | 1/2021 | Shemesh et al. | |
| 10,898,139 B2 | 1/2021 | Guta et al. | |
| 10,905,329 B2 | 2/2021 | Bar-Tal et al. | |
| 10,912,484 B2 | 2/2021 | Ziv-Ari et al. | |
| 10,918,306 B2 | 2/2021 | Govari et al. | |
| 10,939,871 B2 | 3/2021 | Altmann et al. | |
| 10,952,795 B2 | 3/2021 | Cohen et al. | |
| 10,973,426 B2 | 4/2021 | Williams et al. | |
| 10,973,461 B2 | 4/2021 | Baram et al. | |
| 10,987,045 B2 | 4/2021 | Basu et al. | |
| 11,006,902 B1 | 5/2021 | Bonyak et al. | |
| 11,040,208 B1 | 6/2021 | Govari et al. | |
| 11,045,628 B2 | 6/2021 | Beeckler et al. | |
| 11,051,877 B2 | 7/2021 | Sliwa et al. | |
| 11,109,788 B2 | 9/2021 | Rottmann et al. | |
| 11,116,435 B2 | 9/2021 | Urman et al. | |
| 11,129,574 B2 | 9/2021 | Cohen et al. | |
| 11,160,482 B2 | 11/2021 | Solis | |
| 11,164,371 B2 | 11/2021 | Yellin et al. | |
| 2001/0005792 A1 | 6/2001 | Steglich | |
| 2002/0065455 A1 | 5/2002 | Ben-Haim et al. | |
| 2003/0120150 A1 | 6/2003 | Govari | |
| 2003/0220578 A1* | 11/2003 | Ho | A61B 5/352 |
| | | | 600/521 |
| 2004/0068178 A1 | 4/2004 | Govari | |
| 2004/0210121 A1 | 10/2004 | Fuimaono et al. | |
| 2006/0009689 A1 | 1/2006 | Fuimaono et al. | |
| 2006/0009690 A1 | 1/2006 | Fuimaono et al. | |
| 2006/0100669 A1 | 5/2006 | Fuimaono et al. | |
| 2007/0066876 A1* | 3/2007 | Hallin | A61B 5/296 |
| | | | 600/301 |
| 2007/0093806 A1 | 4/2007 | Desai et al. | |
| 2007/0276212 A1 | 11/2007 | Fuimaono et al. | |
| 2008/0234564 A1 | 9/2008 | Beatty et al. | |
| 2009/0221897 A1 | 9/2009 | Nieuwkoop | |
| 2010/0010583 A1 | 1/2010 | Panken et al. | |
| 2010/0268038 A1* | 10/2010 | Smith | A61B 5/0215 |
| | | | 600/300 |
| 2011/0118726 A1 | 5/2011 | De La Rama et al. | |
| 2011/0160574 A1 | 6/2011 | Harlev et al. | |
| 2011/0190625 A1 | 8/2011 | Harlev et al. | |
| 2011/0245756 A1 | 10/2011 | Arora et al. | |
| 2011/0301597 A1 | 12/2011 | McDaniel et al. | |
| 2013/0172872 A1 | 7/2013 | Subramaniam et al. | |
| 2013/0172883 A1 | 7/2013 | Lopes et al. | |
| 2013/0178850 A1 | 7/2013 | Lopes et al. | |
| 2013/0190587 A1 | 7/2013 | Lopes et al. | |
| 2013/0296852 A1 | 11/2013 | Madjarov et al. | |
| 2014/0025069 A1 | 1/2014 | Willard et al. | |
| 2014/0052118 A1 | 2/2014 | Laske et al. | |
| 2014/0081114 A1 | 3/2014 | Shachar et al. | |
| 2014/0121470 A1* | 5/2014 | Scharf | A61B 8/445 |
| | | | 600/301 |
| 2014/0180147 A1 | 6/2014 | Thakur et al. | |
| 2014/0180151 A1 | 6/2014 | Maskara et al. | |
| 2014/0180152 A1 | 6/2014 | Maskara et al. | |
| 2014/0257069 A1 | 9/2014 | Eliason et al. | |
| 2014/0276712 A1 | 9/2014 | Mallin et al. | |
| 2014/0309512 A1 | 10/2014 | Govari et al. | |
| 2015/0011991 A1 | 1/2015 | Buysman et al. | |
| 2015/0045863 A1 | 2/2015 | Litscher et al. | |
| 2015/0066122 A1* | 3/2015 | Govea | A61N 1/05 |
| | | | 607/116 |
| 2015/0080693 A1 | 3/2015 | Solis | |
| 2015/0105770 A1 | 4/2015 | Amit | |
| 2015/0119878 A1 | 4/2015 | Heisel et al. | |
| 2015/0133919 A1 | 5/2015 | McDaniel et al. | |
| 2015/0208942 A1 | 7/2015 | Bar-Tal et al. | |
| 2015/0250424 A1 | 9/2015 | Govari et al. | |
| 2015/0270634 A1 | 9/2015 | Buesseler et al. | |
| 2015/0342532 A1 | 12/2015 | Basu et al. | |
| 2015/0351652 A1 | 12/2015 | Marecki et al. | |
| 2016/0081746 A1 | 3/2016 | Solis | |
| 2016/0113582 A1 | 4/2016 | Altmann et al. | |
| 2016/0113709 A1 | 4/2016 | Maor | |
| 2016/0183877 A1 | 6/2016 | Williams et al. | |
| 2016/0228023 A1 | 8/2016 | Govari | |
| 2016/0228062 A1 | 8/2016 | Altmann et al. | |
| 2016/0242667 A1 | 8/2016 | Fay et al. | |
| 2016/0278853 A1 | 9/2016 | Ogle et al. | |
| 2016/0302858 A1 | 10/2016 | Bencini | |
| 2016/0317093 A1 | 11/2016 | Berenfeld et al. | |
| 2016/0338770 A1 | 11/2016 | Bar-Tal et al. | |
| 2017/0027638 A1 | 2/2017 | Solis | |
| 2017/0042449 A1* | 2/2017 | Deno | A61B 5/341 |
| 2017/0065227 A1 | 3/2017 | Marrs et al. | |
| 2017/0071543 A1 | 3/2017 | Basu et al. | |
| 2017/0071544 A1 | 3/2017 | Basu et al. | |
| 2017/0071665 A1 | 3/2017 | Solis | |
| 2017/0095173 A1 | 4/2017 | Bar-Tal et al. | |
| 2017/0100187 A1 | 4/2017 | Basu et al. | |
| 2017/0143227 A1 | 5/2017 | Marecki et al. | |
| 2017/0156790 A1 | 6/2017 | Aujla | |
| 2017/0172442 A1 | 6/2017 | Govari | |
| 2017/0185702 A1 | 6/2017 | Auerbach et al. | |
| 2017/0202515 A1 | 7/2017 | Zrihem et al. | |
| 2017/0221262 A1 | 8/2017 | Laughner et al. | |
| 2017/0224958 A1 | 8/2017 | Cummings et al. | |
| 2017/0265812 A1 | 9/2017 | Williams et al. | |
| 2017/0281031 A1 | 10/2017 | Houben et al. | |
| 2017/0281268 A1 | 10/2017 | Tran et al. | |
| 2017/0296125 A1 | 10/2017 | Altmann et al. | |
| 2017/0296251 A1 | 10/2017 | Wu et al. | |
| 2017/0347959 A1 | 12/2017 | Guta et al. | |
| 2017/0354338 A1 | 12/2017 | Levin et al. | |
| 2017/0354339 A1 | 12/2017 | Zeidan et al. | |
| 2017/0354364 A1 | 12/2017 | Bar-Tal et al. | |
| 2018/0008203 A1 | 1/2018 | Iyun et al. | |
| 2018/0028084 A1 | 2/2018 | Williams et al. | |
| 2018/0049803 A1 | 2/2018 | Solis | |
| 2018/0085064 A1 | 3/2018 | Auerbach et al. | |
| 2018/0132749 A1 | 5/2018 | Govari et al. | |
| 2018/0137687 A1 | 5/2018 | Katz et al. | |
| 2018/0160936 A1* | 6/2018 | Govari | A61B 18/1492 |
| 2018/0160978 A1 | 6/2018 | Cohen et al. | |
| 2018/0168511 A1 | 6/2018 | Hall et al. | |
| 2018/0184982 A1 | 7/2018 | Basu et al. | |
| 2018/0192958 A1 | 7/2018 | Wu | |
| 2018/0206792 A1 | 7/2018 | Auerbach et al. | |
| 2018/0235692 A1 | 8/2018 | Efimov et al. | |
| 2018/0249959 A1 | 9/2018 | Osypka | |
| 2018/0256109 A1 | 9/2018 | Wu et al. | |
| 2018/0256248 A1 | 9/2018 | Bae et al. | |
| 2018/0279954 A1 | 10/2018 | Hayam et al. | |
| 2018/0303362 A1* | 10/2018 | Koertge | A61B 5/0024 |

(56) References Cited

U.S. PATENT DOCUMENTS

| | | |
|---|---|---|
| 2018/0303414 A1 | 10/2018 | Toth et al. |
| 2018/0310987 A1 | 11/2018 | Altmann et al. |
| 2018/0311497 A1 | 11/2018 | Mswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Mswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Mswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0187808 A1* | 6/2020 | Yang ............... A61B 5/0008 |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Mswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| CN | 111248993 A | 6/2020 |
| CN | 111248996 A | 6/2020 |
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| JP | 2017511166 A | 4/2017 |
| WO | 9421167 A1 | 9/1994 |
| WO | 9421169 A1 | 9/1994 |
| WO | WO 96/05768 A1 | 2/1996 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |

(56) References Cited

FOREIGN PATENT DOCUMENTS

| WO | 2019143960 A1 | 7/2019 |
| WO | 2020026217 A1 | 2/2020 |
| WO | 2020206328 A1 | 10/2020 |

OTHER PUBLICATIONS

Extended European Search Report dated May 28, 2020, from corresponding EP Application No. 19219607.9.
Horner S M et al: 11 Electrode for recording direction of activation, conduction velocity, and monophasic action potential of myocardium, American Journal of Physiology: Heart and Circulatory Physiology, American Physiological Society, US, vol. 272, No. 4 41-4, Apr. 1, 1997 (Apr. 1, 1997), pp. H1917-H1927, XP008169988, ISSN: 0363-6135 * section "Methods"; figures 1-3.
Notification of Reasons for Refusal dated Jul. 25, 2023, from corresponding Japanese Application No. 2019-237790.
English translation of First Office Action dated May 31, 2023, from corresponding Chinese Application No. CN201911377849.X.
Extended European Search Report and Opinion dated Oct. 9, 2024, from corresponding EP Application No. 24172946.6.
English translation of Written Opinion dated Oct. 20, 2023, from corresponding Japanese Application No. 2019-237790.
English translation of Notice of Reasons for Refusal dated Jan. 16, 2024, from corresponding Japanese Application No. 2019-237790.
English translation of Written Opinion dated Apr. 15, 2024, from corresponding Japanese Application No. 2019-237790.
English translation of Decision to Grant a Patent dated Jul. 2, 2024, from corresponding Japanese Application No. 2019-237790.

\* cited by examiner

MAPPING ECG SIGNALS USING A MULTIPOLE ELECTRODE ASSEMBLY

CROSS-REFERENCE TO RELATED APPLICATION

This application is a continuation of U.S. patent application Ser. No. 16/235,769, filed 28 Dec. 2018, and granted as U.S. Pat. No. 11,207,016, the contents of which are incorporated herein by reference as if presented in full.

FIELD OF THE INVENTION

The present invention relates generally to medical devices, and particularly to methods and systems for mapping anatomical signals in a patient body.

BACKGROUND OF THE INVENTION

Various methods for measuring anatomical signals, such as electrocardiogram (ECG) signals are known in the art.

For example, U.S. Patent Application Publication 2009/0221897 describes a sensor for measuring electrical variables at the surface of a human or animal body. The sensor comprising three of more electrodes in a geometrically regular arrangement, and a support member arranged to keep the electrodes together.

U.S. Patent Application Publication 2010/0010583 describes techniques for posture classification of a patient in a coordinate system of a sensor. A defined vector is obtained from a sensor disposed in a substantially fixed manner relative to the patient, the defined vector is described in a coordinate system of the sensor and without regard to an orientation in which the sensor is disposed in relation to the patient. A detected vector is obtained from the sensor that is described using the coordinate system of the sensor. The detected vector and the defined vector to are used to classify the posture state of the patient without regard to the orientation in which the sensor is disposed in relation to the patient.

SUMMARY OF THE INVENTION

An embodiment of the present invention that is described herein provides a medical probe including an insertion tube for insertion into a patient body, at least an arm, which is attached to a distal end of the insertion tube, at least a reference electrode coupled to the arm, and multiple electrodes, which are coupled to the arm, surround the reference electrode and are configured to sense electrical signals of body tissues that, when measured relatively to the reference electrode, are indicative of anatomical signals in the patient body.

In some embodiments, the electrodes are arranged in a non-uniform geometry around the reference electrode. In other embodiments, the anatomical signals include electrocardiogram (ECG) signals. In yet other embodiments, the medical probe includes electrical conductors, which are electrically connected to one or more of the electrodes and are configured to transmit the electrical signals to a system external to the patient body.

In an embodiment, the medical probe includes one or more wireless communication devices, which are electrically connected to one or more of the electrodes and are configured to transmit the electrical signals to a system external to the patient body. In another embodiment, the arm includes a flexible printed circuit board (PCB).

In some embodiments, the electrical signals are indicative of a direction of the anatomical signals. In other embodiments, the electrical signals are indicative of a propagation speed of the anatomical signals.

There is additionally provided, in accordance with an embodiment of the present invention, a method that includes, receiving electrical signals from a medical probe, which includes: (a) at least an arm, which is attached to a distal end of an insertion tube, (b) at least a reference electrode coupled to the arm, and (c) multiple electrodes, which are coupled to the arm, surround the reference electrode, and produce the electrical signals. The electrical signals, when measured relatively to the reference electrode, are indicative of a direction of anatomical signals in the patient body. Based on the electrical signals, at least one of a direction and a propagation speed of the anatomical signals is estimated.

There is additionally provided, in accordance with an embodiment of the present invention, a method for producing a medical probe, the method includes, attaching, to a distal end of an insertion tube, at least an arm. At least a reference electrode is coupled to the arm. Multiple electrodes arranged in a non-uniform geometry and surrounding the reference electrode are coupled to the arm.

There is further provided, in accordance with an embodiment of the present invention, a system that includes a reference electrode, a medical probe that includes an insertion tube for insertion into a patient body, at least an arm, which is attached to a distal end of the insertion tube, and multiple electrodes, which are coupled to the arm, and are configured to sense electrical signals of body tissues that, when measured relative to the reference electrode, are indicative of anatomical signals in the patient body. The system further includes a processor, which is configured to estimate, based on the electrical signals, at least one of a direction and a propagation speed of the anatomical signals.

In some embodiments, the reference electrode includes a body surface electrode coupled to a skin of the patient body. In other embodiments, the reference electrode includes a virtual electrode having a reference signal, and the processor is configured to calculate the reference signal based on additional electrical signals received from at least two body surface electrodes coupled to a skin of the patient body.

In an embodiment, the reference signal is calculated by averaging the additional electrical signals of at least two of the body surface electrodes. In another embodiment, the reference electrode is coupled to the arm, and the multiple electrodes surround the reference electrode.

The present invention will be more fully understood from the following detailed description of the embodiments thereof, taken together with the drawings in which:

DETAILED DESCRIPTION OF EMBODIMENTS

Overview

Embodiments of the present invention that are described hereinbelow provide improved methods and systems for estimating the direction and propagation speed of wavefronts caused by anatomical signals, such as electrocardiogram (ECG) signals, in a patient body. In some embodiments, a system for estimating the direction and propagation speed of wavefronts caused by the ECG signals comprises a minimally invasive probe having a distal-end assembly coupled to an insertion tube, and a processor. The distal-end assembly comprises multiple spines, also referred to as arms, wherein each spine comprises a strip made from a flexible printed circuit board (PCB).

In some embodiments, each spine comprises multiple electrode assemblies coupled to the circuit board side facing the patient tissue, wherein the PCB comprises conductors that provide electrical connectivity between the electrode assemblies and conducting elements, such as traces or wiring running through the probe to a system external to the patient body.

In some embodiments, each electrode assembly comprises multiple electrodes arranged in a non-uniform geometry. The electrodes are configured to sense electrical signals of body tissues that, when measured relatively to another electrode of the electrode assembly, are indicative of the direction and magnification of the ECG signals in the patient heart.

In some embodiments, at least one of the electrodes comprises a reference electrode, wherein the other electrodes of the assembly are surrounding the reference electrode and may be arranged in a uniform or non-uniform geometry.

In some embodiments, the probe is typically inserted into the patient body in a collapsed position (e.g., using a sheath) and is extended upon reaching a target location such as a cavity of the patient heart. In the extended position, the spines are extended to conform to the shape of the cavity so that the electrodes coupled to the spines make contact with the tissue of the inner cavity surface and produce electrical signals indicative of the sensed ECG signals. These electrical signals are provided to the processor.

In some embodiments, the electrode assembly comprises multiple dipoles formed by the arrangement of the electrodes in a multipole configuration. The multipole arrangement is configured to sense the ECG signals in any direction in the patient heart.

In some embodiments, the processor is configured to estimate, based on the electrical signals, the direction and propagation speed of the ECG signals. The processor is configured to use various methods, such as calculating vector components of every dipole, and calculating vector addition and/or vector subtraction between the dipoles so as to estimate the direction and speed of a wavefront that carries the electrical field produced by the ECG signals.

The disclosed techniques improve the accuracy and sensitivity of ECG mapping in patient heart, for diagnosing and treating arrhythmia and other cardiac diseases. Moreover, the disclosed techniques may also be used for accurate mapping of other anatomical signals in patient organs.

System Description

Figure 1:
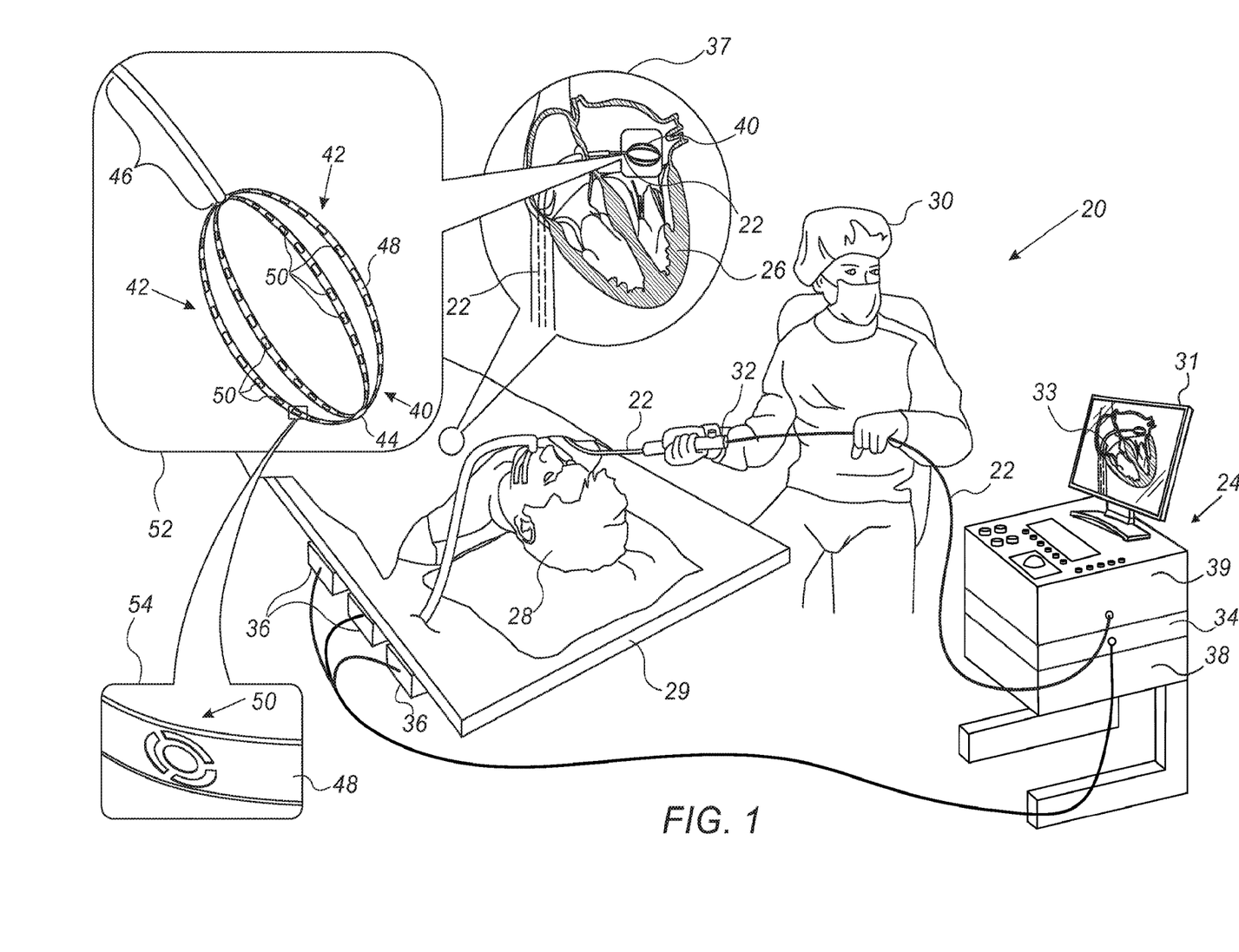
FIG. 1 is a schematic, pictorial illustration of a catheter tracking system, in accordance with an embodiment of the present invention.

FIG. 1 is a schematic, pictorial illustration of a catheter tracking system 20, in accordance with an embodiment of the present invention. System 20 comprises a probe, in the present example a cardiac catheter 22, and a control console 24. In the embodiment described herein, catheter 22 may be used for any suitable therapeutic and/or diagnostic purposes, such as mapping of electro-cardiac signals for the diagnosis of cardiac dysfunctions, such as cardiac arrhythmias, and/or ablation of tissue in a heart 26, e.g., based on the mapping described above.

Console 24 comprises a processor 39, typically a general-purpose processor of a general-purpose computer, with suitable front end and interface circuits for receiving signals from catheter 22 and for controlling the other components of system 20 described herein. Processor 39 may be programmed in software to carry out the functions that are used by the system, and the processor stores data for the software in a memory 38. The software may be downloaded to console 24 in electronic form, over a network, for example, or it may be provided on non-transitory tangible media, such as optical, magnetic or electronic memory media. Alternatively, some or all of the functions of processor 39 may be carried out by dedicated or programmable digital hardware components.

An operator 30 (such as an interventional cardiologist) inserts catheter 22 through the vascular system of a patient 28 lying on a table 29. Catheter 22 comprises an insertion tube (not shown), and a distal-end assembly 40 that comprises multiple spines, also referred to herein as "splines" or "arms" (shown in inset 52 and described in detail below). Operator 30 moves assembly 40 of catheter 22 in the vicinity of the target region in heart 26 by manipulating catheter 22 with a manipulator 32 near the proximal end of the catheter as shown in an inset 37 of FIG. 1. The proximal end of catheter 22 is connected to interface circuitry of processor 39 so as to exchange electrical signals therewith.

The position of the distal-end assembly in the heart cavity is typically measured by magnetic position sensing in catheter tracking system 20. In this case, console 24 comprises a driver circuit 34, which drives magnetic field generators 36 placed at known positions external to patient 28 lying on table 29, e.g., below the patient's torso.

Distal-end assembly 40 typically comprises multiple spines, each comprising one or more magnetic field sensors and/or one or more ablation or mapping electrodes, and/or other devices (as shown, for example in inset 52 and in FIGS. 2, 3A, 3B and 3C below). When the distal-end assembly is brought into contact with the intracardiac tissue, e.g., the inner heart surface, the mapping electrodes generate potential gradient signals in response to the sensed electrical potentials, also referred to herein as electrical signals.

In some embodiments, the position sensors generate position signals in response to the sensed external magnetic fields, thereby enabling processor 39 to map the electrical potentials as a function of position within the heart cavity. In some embodiments, the sensed electrical signals are indicative of a direction and propagation speed of wavefronts caused by anatomical signals, such as electrocardiogram (ECG) signals in heart 26, as will be described in detail in FIG. 2 below.

The multiple magnetic position sensors and mapping electrodes of assembly 40 are connected to interface circuitry of processor 39 at the catheter proximal end. Operator 30 can view the position of assembly 40 in an image 33 of heart 26 on a user display 31.

This method of position sensing is implemented, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In other embodiments, instead of magnetic position sensors, distal end assembly 40 may comprise one or more impedance position sensors, such as advanced current localization (ACL) sensors, or any other suitable position sensors, and system 20 may comprise a respective position tracking module. In alternative embodiments, system 20 does not comprise any position tracking module, and distal end assembly 40 does not comprise any position tracking sensors.

Basket Catheter for Sensing ECG Signals in Patient Heart

Reference is now made to inset 52. In some embodiments, each spine 42 is coupled to a cap 44 located at the distal tip of distal end assembly 40. In some embodiments, catheter 22 further comprises a shaft 46, which is used for the transition of assembly 40 between the collapsed and extended positions. For example, after inserting catheter 22 into heart 26, shaft 46 is configured to extract distal end assembly 40 out of a sheath (not shown) so as to bring assembly 40 to an extended position. Similarly, after concluding the medical procedure, shaft 46 is configured to retract distal end assembly 40 into the sheath to the collapsed position, typically before retracting catheter 22 out of patient body.

In some embodiments, multiple electrode assemblies 50 are formed on an external surface of a flexible printed circuit board (PCB) 48 so that in the extended position of distal end assembly 40, electrode assemblies 50 make contact with the tissue of heart 26. Other components, such as sensors, may be coupled to the spine in a similar manner.

In some embodiments, electrical circuit traces (not shown) are formed in PCB 48 of spine 42, each trace is connected to at least one electrode of each electrode assembly 50. In some embodiments, the electrical circuit traces are connected to suitable wiring or other types of electrical conductors that runs through catheter 22, for exchanging signals between console 24 and electrode assemblies 50.

Reference is now made to an inset 54. In some embodiments, each electrode assembly 50 comprises at least three electrodes. In the example of inset 54 assembly 50 comprises a reference electrode coupled to spine 52 and three electrodes, which are also coupled to the respective spine, surround the reference electrode and are configured to sense electrical signals of body tissues that, when measured relatively to the reference electrode, are indicative of the aforementioned direction and propagation speed of wavefronts caused by the ECG signals in heart 26. Additional embodiments related to the structure and operation of electrode assembly 50 are described in detail in FIGS. 2, 3A, 3B and 3C below. Additionally or alternatively, the electrodes of electrode assembly 50 are configured to sense electrical signals indicative of the direction and speed of any other anatomical signals moving in the patient body.

In other embodiments, distal end assembly 40 may comprise one or more wireless communication device (not shown), which are electrically connected to one or more of the electrodes of electrode assembly 50. The one or more wireless communication devices are configured to transmit the electrical signals to console 24 or to any other system external to the patient body.

Sensing the Speed and Direction of ECG Signals Propagating in Patient Heart

Figure 2:
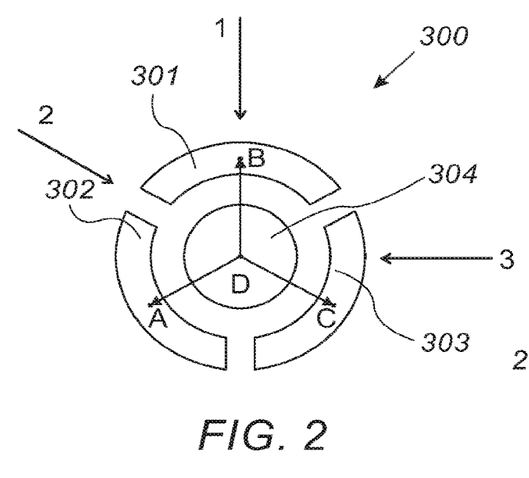
FIGS. 2 and 3A-3C are schematic, pictorial illustrations of several configurations of electrode assemblies that can be used for measuring a direction and propagation speed of a wavefront of anatomical signals in a patient heart, in accordance with embodiments of the present invention.

FIG. 2 is a schematic, pictorial illustration of an electrode assembly 300 configured to measure the direction and propagation speed of a wavefront caused by ECG signals in heart 26, in accordance with an embodiment of the present invention. Electrode assembly 300 may replace, for example, electrode assembly 50 of FIG. 1 above, and is configured to sense ECG signals or any other signals in the body of patient 28.

In some embodiments, electrode assembly 300 comprises three electrodes 301, 302 and 303 and a reference electrode 304, which are coupled to or embedded in PCB 48 of spine 42. Electrodes 301-303 surround reference electrode 304 and may be arranged in a uniform or non-uniform geometry around reference electrode 304.

In an embodiment, electrodes 301, 302, 303 and 304 whose respective centers of gravity (COGs) are denoted "A," "B," "C" and "D" in the figure, are arranged in three dipoles between reference electrode 304 and each of electrodes 301, 302 and 303, and are shown as vectors DA, DB and DC, respectively. In this configuration, vector DA shows the dipole between reference electrode 304 and electrode 302, vector DB shows the dipole between reference electrode 304 and electrode 301, and vector DC shows the dipole between reference electrode 304 and electrode 303.

Three examples of wavefronts, which are caused by three respective ECG signals of heart 26, are shown in FIG. 2, and are referred to herein as wavefronts "1," "2" and "3." It will be understood that the propagation of wavefronts "1," "2" and "3" carry electrical fields along the tissue of heart 26 and typically only one of these example wavefronts exists at a time.

Note that for a time period, the changes in voltages sensed by the electrodes of a given dipole is indicative of the wavefront propagation speed. Information combined from two or more dipoles, allows for determination of the wavefront propagation direction, which is defined, for example, in a Cartesian coordinate system.

In the example of FIG. 2, the COG of reference electrode 304 is aligned with the COG (not shown) of electrode assembly 300. In addition, electrodes 301-303 share a similar shape that differs from the shape of reference electrode 304. In some embodiments, the shapes of electrodes 301-303 may be chosen to maximize circumferential coverage around reference electrode 304, while also matching surface areas so each dipole is comprised of two electrodes of equal surface area.

In some embodiments, electrodes 301-304 may be arranged in any suitable geometric structure, which may be regular or non-regular. The terms "non-regular" and "irregular" may refer to a structure in which the COGs of electrodes 301, 302, 303, and 304 do not lie on the same geometrical plane. As described above, the non-regular geometrical arrangement allows sensing a wavefront moving in any direction, such as the directions of wavefronts "1," "2" or "3" or any other direction.

In some embodiments, processor 39 is configured to receive electrical signals produced by electrodes 301-304 (e.g., voltage of each electrode 301-303 relative to reference electrode 304), which are indicative of the direction and speed of the wavefront caused by the ECG signals in heart 26.

In some embodiments, in response to wavefront "1," the dipole represented by vector DB, which is substantially parallel to wavefront "1" and having the inverse direction, will at a first time, t1 sense the most negative value of voltage among all the dipoles. The dipoles represented by vectors DA and DC will sense, at a second later time, t2, a positive value of voltage.

In an example embodiment, in response to wavefront "2," the dipole represented by vector DB will sense, at a first time, t1, a negative value of voltage. The dipole represented by vector DA will sense at a second later time t1+δ a similar negative value of voltage. Finally, the dipole represented by vector DC, which is substantially parallel to wavefront "2," will sense, at a third later time, t2, a positive value of voltage. The timing difference between when the dipole represented by vector DB and the dipole represented by vector DA first sense voltage changes (δ) can be used to determine the direction of wavefront "2." For example, a greater value of δ would correspond to a wavefront which was closer to wavefront "1", a δ of zero would correspond to a wavefront anti-parallel to vector DC, and a negative value of δ would correspond to a wavefront that is closer to being anti-parallel to vector DA.

In an embodiment, in response to wavefront "3," the dipole represented by vector DC will sense at a first time t1, a negative value of voltage. The dipole represented by vector DB, which is substantially orthogonal to wavefront "3," will sense, at a second later time, t2, a negative value of voltage. Subsequently, at a third time, t3, the dipole represented by vector DA will sense a positive value of voltage.

In some embodiments, based on these electrical signals, processor 39 is configured to estimate the direction and speed of the wavefront caused by the ECG signals in heart 26. The change in the value of the sensed voltage is indicative of the speed of the wavefront and based on a combination of signals from two or more of the aforementioned dipoles, processor 39 may calculate the direction, as well as the speed, of the wavefront caused by the ECG signals of heart 26.

In other embodiments, electrodes 301, 302, 303, and 304 may have any other suitable type of non-regular geometrical arrangement. For example, at least two of electrodes 301, 302, and 303 may have a unique geometrical shape, and/or size and/or geometrical orientation that differs from one another. Additionally or alternatively, the distances between COGs of the aforementioned dipoles may differ from one another. In the example of FIG. 2, vectors DA and DB may have different respective lengths, for example.

In other embodiments, electrode assembly 300 may comprise any other suitable number of electrodes arranged in any suitable irregular geometrical structure. In these embodiments, the electrode assembly may have any suitable shape, symmetric or asymmetric. For example, the shape of the electrode assembly may be non-round or even non-circular. Note that at least one of the non-regular arrangements described above may be used to increase the sensitivity of the electrode assembly to sense ECG signals in predefined directions.

In some embodiments, processor 39 may hold calibration data (e.g., stored in a file) for each electrode assembly having a non-regular structure as described above. Based on the calibration data, processor 39 is configured to compensate for the shape irregularity in the calculation of the direction and propagation speed of the wavefronts.

Figure 3A:
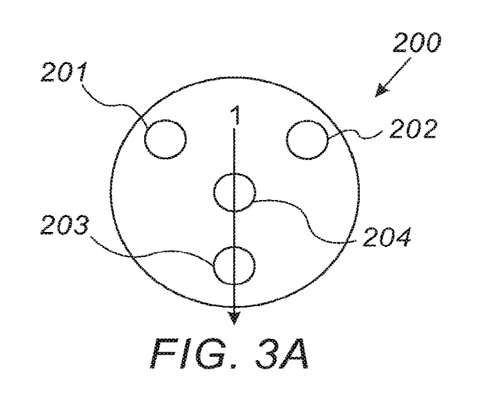

FIG. 3A is a schematic, pictorial illustration of an electrode assembly 200 configured to measure the direction and propagation speed of wavefronts caused by anatomical signals in heart 26, in accordance with another embodiment of the present invention. Electrode assembly 200 may replace, for example, electrode assembly 50 of FIG. 1 above, and is configured to sense wavefronts caused by ECG signals or any other signals in the body of patient 28.

In some embodiments, electrode assembly 200 comprises three electrodes 201, 202 and 203 and a reference electrode 204, which are coupled to or embedded in PCB 48 of spine 42. Electrodes 201-203 surround reference electrode 204 and may be arranged in a uniform or non-uniform geometry around reference electrode 204. As described in FIG. 2 above, electrodes 201, 202 and 203 and a reference electrode 204 are arranged in three dipoles, a first dipole between reference electrode 204 and electrode 201, a second dipole between reference electrode 204 and electrode 202, and a third dipole between reference electrode 204 and electrode 203. In the example of FIG. 3A, the COG of reference electrode 204 is aligned with the COG of electrode assembly 200 (not shown), and the shape and surface area of electrodes 201-204 is similar.

Figure 3B:
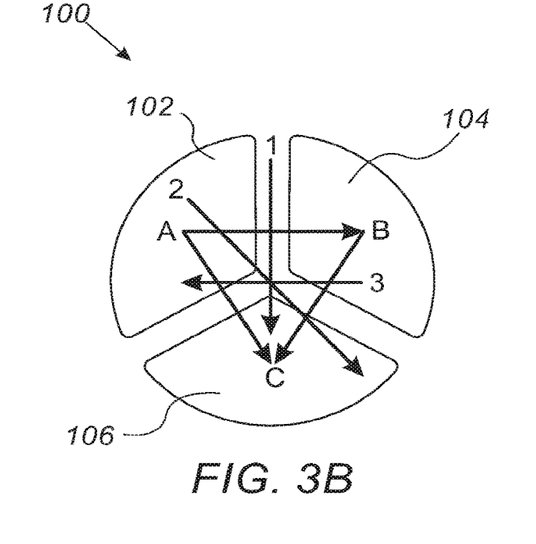
Figure 3C:
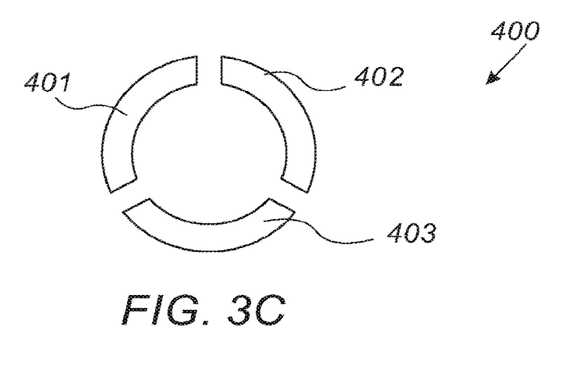

In the context of the present invention and in the claims, the terms "non-uniform," "non-regular" and "non-periodic" are used interchangeably, and refer to any of the geometrical arrangements described in FIG. 2 above, in FIGS. 3A, 3B and 3C, and/or to a geometrical structure in which the COG of reference electrode 204 is not located on a straight line connecting between any pair of electrodes from among electrodes 201-203.

Moreover, in an example of a round-shaped electrode assembly, but in contrast to the configuration of electrode assembly 200, the COG of the reference electrode may be not aligned with the COG of the electrode assembly.

Additionally or alternatively, at least one of electrodes 201-204 may have a different size, shape and/or surface area compared to the other electrodes, e.g., electrode 204 may be larger than electrodes 201-203.

In some embodiments, electrodes 201-203 are configured to sense electrical signals of body tissues that, when measured relatively to reference electrode 204, are indicative of the direction and speed of the wavefront caused by the ECG signals in heart 26, as described in FIG. 2 above.

In some embodiments, electrodes 201-203 and 204 are electrically connected to processor 39 via the electrical traces and wiring of catheter 22, or via the wireless device, as described in FIGS. 1 and 2 above.

In some embodiments, processor 39 is configured to receive the electrical signals produced by the aforementioned dipoles of electrode assembly 200, and to estimate, based on the electrical signals, the direction and speed of a wavefront propagating in heart 26.

In some embodiments, processor 39 compares the voltage measured by each of electrodes 201-203 relative to reference electrode 204. Based on the comparison, processor 39 may estimate the direction and speed of a propagating wavefront caused by the ECG signals. For example, in response to wavefront "1," which is orthogonal to a virtual line (not shown) connecting between electrodes 201 and 202, the voltage changes would first be sensed by a dipole comprising electrodes 201 and 204 and by a dipole comprising electrodes 202 and 204, and later by a dipole comprising electrodes 203 and 204. As described in FIG. 2 above, based on the timing and values of these sensed voltages, processor 39 may estimate the direction and propagation speed of wavefront "1" caused by the ECG signals in heart 26. Techniques to allow for the estimating or determination of the direction and speed of the wavefront are shown and described at pages 5-10 and specifically page 7 of "TECHNIQUES FOR AUTOMATED LOCAL ACTIVATION TIME ANNOTATION AND CONDUCTION VELOCITY ESTIMATION IN CARDIAC MAPPING" by C. D. Cantwell, C. H. Roney, F. S. Ng, J. H. Siggers, S. J. Sherwina, N. S. Peters, published in Computers in Biology and Medicine, April 2015, which article is incorporated by reference with a copy attached hereto in the Appendix.

FIG. 3B is a schematic, pictorial illustration of an electrode assembly 100, configured to measure the direction and propagation speed of a wavefront propagating in heart 26, in accordance with another embodiment of the present invention. Electrode assembly 100 may replace, for example, electrode assembly 50 of FIG. 1 above.

In some embodiments, electrode assembly 100 comprises three electrodes 102, 104 and 106, each of which having a wedge shape and is positioned at a predefined distance from the other two electrodes. In some embodiments, electrodes 102, 104 and 106 are arranged geometrically such that electrode assembly 100 has a round shape.

In some embodiments, electrodes 102, 104 and 106 are coupled to PCB 48 of spine 42 (as shown in FIG. 1) and are electrically connected to processor 39 via the aforementioned electrical traces and wiring, or via the wireless device, as described in FIG. 1 above.

In some embodiments, electrode assembly 100 comprises three electrodes and, unlike electrode assemblies 300 and 200 of respective FIGS. 2 and 3A above, does not comprise a reference electrode.

In an embodiment, electrodes 102, 104 and 106 whose respective COGs are denoted "A," "B" and "C" in the figure, are arranged in three dipoles between each pair of these electrodes, A-B, A-C and B-C. In some embodiments, in response to any wavefront, such as the aforementioned wavefronts "1," "2," or "3," a vector "AB" is indicative of a voltage sensed by dipole A-B comprising electrodes 102 and 104. Similarly, a vector "BC" is indicative of a voltage sensed by dipole B-C comprising electrodes 104 and 106, and a vector "AC" is indicative of a voltage sensed by dipole A-C comprising electrodes 102 and 106.

In some embodiments, in response to wavefront "1," which is orthogonal to vector AB, electrodes 102 and 104 sense about the same signals, thus, the voltage sensed, at a first time, t1, by the dipole represented by the vector AB, is about zero. Subsequently, the other two dipoles represented by vectors AC and BC sense, at a later time, t2, similar (e.g., positive) values of voltage. In some embodiments, processor 39 is configured to estimate, based on the timing and voltages sensed by dipoles A-B, A-C and B-C, the direction and speed of wavefront "1."

In an example embodiment, in response to wavefront "2," the dipole represented by vector AC, which is almost parallel to wavefront "2" and having the same direction, will at a first time, t1 sense a positive value of voltage, and the dipole represented by vector BC, which is almost orthogonal to wavefront "2" will sense a positive value of voltage at a second later time, t2.

In another example embodiment, in response to wavefront "3," the dipole represented by vector AB, which is substantially parallel to wavefront "3" and having an opposite direction, will sense, at time t1, a negative value of voltage. Based on the embodiments and definitions described above, the dipole represented by vector BC will sense a positive value of voltage at time t1. Subsequently, at a third later time, t3, the dipole represented by vector AC will sense a negative value of voltage.

In some embodiments, processor 39 is configured to estimate the direction and speed of any wavefronts based on the timing of the sensed voltages received from the three dipoles, as described in FIG. 2 above. Estimating the direction and speed of the wavefront may be carried out using vector addition, vector subtraction or both. Alternatively any other suitable method of calculation for estimating the direction and speed can be used.

In some embodiments, electrodes 102, 104 and 106 may be arranged in any suitable geometric structure, which may be regular or non-regular. The terms "non-regular" and "irregular" may refer to a structure in which the COGs of electrodes 102, 104 and 106 do not lie on the same geometrical plane. As described above, the non-regular geometrical arrangement allows sensing a wavefront moving in any direction, such as the directions of wavefronts "1," "2," or "3" or any other direction.

In other embodiments, electrodes 102, 104 and 106 may have any other suitable type of non-regular geometrical arrangement. For example, at least two of electrodes 102, 104 and 106 may have a unique geometrical shape, and/or size and/or geometrical orientation that differs from one another. Additionally or alternatively, the distances between COGs of the aforementioned dipoles may differ from one another. In the example of FIG. 3B, vectors AB and BC may have different respective lengths, for example.

In the example of FIG. 3B, each of electrodes 102, 104 and 106 covers an area that comprises almost a third of the total area of the round shape of electrode assembly 100. In another embodiment, two electrodes (e.g., electrodes 102 and 104) may each cover, each, almost 40% of the area of electrode assembly 100, and the third electrode (e.g., electrode 106) may cover almost 20% of the area of electrode assembly 100. Note that the terms "almost" are used due to the space between each pair of electrodes from among electrodes 102, 104 and 106, which comprises a share of the area of electrode assembly 100.

In other embodiments, electrode assembly may comprise any other suitable number of electrodes arranged in any suitable irregular geometrical structure. In these embodiments, the electrode assembly may have any suitable shape, symmetric or asymmetric. For example, the shape of electrode assembly 100 may be non-round or even non-circular. Note that at least one of the non-regular arrangements described above may be used to increase the sensitivity of the electrode assembly to sense ECG signals in predefined directions.

In some embodiments, processor 39 may hold calibration data (e.g., stored in a file) for each electrode assembly having a non-regular structure as described above. Based on the calibration data, processor 39 is configured to compensate for the shape irregularity in the calculation of the direction and propagation speed of the wavefronts caused by the ECG signals, or by any other signals of patient 28.

FIG. 3C is a schematic, pictorial illustration of an electrode assembly 400 configured to measure the direction and propagation speed of wavefronts caused by ECG signals in heart 26, in accordance with an embodiment of the present invention. Electrode assembly 400 may replace, for example, electrode assembly 50 of FIG. 1 above, and is configured to sense the aforementioned ECG signals or any other signals in the body of patient 28.

In some embodiments, electrode assembly 400 comprises three electrodes 401, 402 and 403, which are coupled to or embedded in PCB 48 of spine 42. Electrodes 401-403 may be arranged in a uniform or non-uniform geometry as described, for example, in FIG. 3B above.

In some embodiments, processor 39 is configured to receive electrical signals from electrodes 401-403, which are indicative of the direction and propagation speed of wavefronts caused by the ECG signals in heart 26. In some embodiments, the electrical signals may be measured with respect to a reference electrode, also referred to herein as a common electrode, such as a virtual electrode, which is not shown in FIG. 3C.

In some embodiments, the virtual electrode may be calculated from two or more body surface electrodes, which are coupled to a skin of patient 28 using a patch or any other suitable coupling technique. One such example of a virtual electrode would be a Wilson's central terminal (WCT).

In alternative embodiments, the dipoles may be formed between two or more physical electrodes, such as any of electrodes 401-403, and a virtual electrode.

In some embodiments, based on these electrical signals and the techniques described, for example, in FIG. 2 above, processor 39 is configured to estimate the direction and speed of a wavefront (e.g., wavefront "1" of FIG. 2 above) caused by the ECG signals in heart 26.

In alternative embodiments, electrodes 401-403 may be arranged in three dipoles (not shown), a first dipole between electrodes 401 and 402, a second dipole between electrodes 402 and 403, and a third dipole between electrodes 403 and 401. Each of these dipoles is configured to sense electrical signals of body tissues indicative of the sensed values of voltage using the technique described in FIG. 3B above.

The configuration of electrode assemblies 50, 100, 200, 300 and 400 are provided by way of example, for demonstrating an example probe or another device in which any of these electrode assemblies may be integrated and used. Alternatively, any other suitable configurations can also be used, for example, using any suitable number of electrodes and/or reference electrodes having any suitable distances therebetween, applying different shape and size of electrode assemblies and of individual electrode or groups of electrodes within the respective electrode assembly. Furthermore, each electrode may be coupled to any suitable type of device, such as processor or controller, using any type coupling technique, and the signals sensed by the electrodes may be transmitted to the device using any suitable communication technique.

Although the embodiments described herein mainly address sensing the direction and propagation speed of anatomical signals in patient heart, the methods and systems described herein can also be used in other applications, such as in sensing the direction and propagation speed of anatomical signals in any other organ of the patient or on the patient skin.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. A medical probe, comprising:
   an insertion tube for insertion into a patient body;
   an arm attached to a distal end of the insertion tube, the arm comprising a printed circuit board;
   a reference electrode on a surface of the printed circuit board and configured to contact internal tissues, the reference electrode having a first shape; and
   exactly three electrodes, each having a second shape different from the first shape, the exactly three electrodes surrounding the reference electrode such that the exactly three electrodes are configured to sense anatomical signals and provide electrical signals which, when measured relative to the reference electrode, are indicative of the anatomical signals in the patient body,
   the reference electrode and the exactly three electrodes forming an electrode assembly, with the second shape of the exactly three electrodes being an arcuate shape that is not a circle,
   the electrode assembly comprising a center of gravity, and
   a center of gravity of the reference electrode aligning with the center of gravity of the electrode assembly.

2. The medical probe of claim 1, wherein the exactly three electrodes are each arranged on the surface of the printed circuit board.

3. The medical probe of claim 1, wherein the electrical signals are indicative of a direction of the anatomical signals.

4. The medical probe of claim 1, wherein the electrical signals are indicative of a propagation speed of the anatomical signals.

5. The medical probe of claim 1, wherein the electrical signals are indicative of a magnitude of the anatomical signals.

6. The medical probe of claim 1, further comprising at least two body surface electrodes configured to be coupled to a skin of the patient body and configured to produce additional electrical signals.

7. The medical probe of claim 1, further comprising one or more wireless communication devices, which are electrically connected to one or more of the electrodes and are configured to transmit the electrical signals to a system external to the patient body.

8. A method, comprising:
   receiving electrical signals from a medical probe, the medical probe comprising:
      an arm attached to a distal end of an insertion tube, the arm comprising a printed circuit board;
      a reference electrode on a surface of the printed circuit board, the reference electrode having a first shape; and
      exactly three electrodes, each having a second shape different from the first shape, the exactly three electrodes surrounding the reference electrode and configured to provide the electrical signals, which, when measured relative to the reference electrode, are indicative of one or more anatomical signals in a patient body,
      the reference electrode and the exactly three electrodes forming an electrode assembly, with the second shape of the exactly three electrodes being an arcuate shape that is not a circle,
      the electrode assembly comprising a center of gravity, and
      a center of gravity of the reference electrode aligning with the center of gravity of the electrode assembly; and
   estimating, based on the electrical signals, the one or more anatomical signals.

9. The method of claim 8, further comprising estimating a direction of the one or more anatomical signals, wherein the electrical signals are indicative of the direction of the one or more anatomical signals.

10. The method of claim 8, further comprising estimating a propagation speed of the one or more anatomical signals, wherein the electrical signals are indicative of the propagation speed of the one or more anatomical signals.

11. The method of claim 8, further comprising estimating a magnitude of the one or more anatomical signals, wherein the electrical signals are indicative of the magnitude of the one or more anatomical signals.

12. The method of claim 8, wherein the each of the exactly three electrodes are on the surface of the printed circuit board.

13. The method of claim 8, wherein the medical probe is configured to receive additional electrical signals from at least two body surface electrodes configured to be coupled to a skin of the patient body.

14. A system, comprising:
a medical probe, comprising:
an insertion tube for insertion into a patient body;
an arm attached to a distal end of the insertion tube, the arm comprising a printed circuit board;
a reference electrode on a surface of the printed circuit board, the reference electrode having a first shape; and
exactly three electrodes, each having a second shape different from the first shape, the exactly three electrodes arranged around the reference electrode and configured to provide electrical signals that, when measured relative to the reference electrode, are indicative of anatomical signals in the patient body, the reference electrode and the exactly three electrodes forming an electrode assembly, with the second shape of the exactly three electrodes being an arcuate shape that is not a circle,
the electrode assembly comprising a center of gravity, and
a center of gravity of the reference electrode aligning with the center of gravity of the electrode assembly; and
a processor configured to estimate, based on the electrical signals, at least one characteristic of the anatomical signals.

15. The system of claim 14, further comprising at least two body surface electrodes configured to be coupled to a skin of the patient body and configured to produce additional electrical signals.

16. The system of claim 14, wherein the processor is configured to calculate a reference signal by averaging electrical signals of at least two body surface electrodes.

17. The system of claim 14, wherein the exactly three electrodes are arranged on the surface of the printed circuit board.

* * * * *